United States Patent
Pallot et al.

(10) Patent No.: US 9,977,027 B2
(45) Date of Patent: May 22, 2018

(54) APPARATUS AND METHOD FOR PREPARING A NINHYDRIN REAGENT

(71) Applicant: AAA Scientific Limited, Greater Manchester (GB)

(72) Inventors: Michael Gerard Pallot, Devon (GB); Leslie John Pitts, Plourac'h (FR); Philip Jones, Devon (GB)

(73) Assignee: AAA Scientific Limited, Greater Manchester (GB)

( * ) Notice: Subject to any disclaimer, the term of this patent is extended or adjusted under 35 U.S.C. 154(b) by 0 days. days.

(21) Appl. No.: 15/318,155

(22) PCT Filed: Jun. 8, 2015

(86) PCT No.: PCT/GB2015/051660
§ 371 (c)(1),
(2) Date: Dec. 12, 2016

(87) PCT Pub. No.: WO2015/189578
PCT Pub. Date: Dec. 17, 2015

(65) Prior Publication Data
US 2017/0242025 A1    Aug. 24, 2017

(30) Foreign Application Priority Data
Jun. 13, 2014 (GB) .................................. 1410633.0

(51) Int. Cl.
*G01N 33/68* (2006.01)
*G01N 21/00* (2006.01)
(Continued)

(52) U.S. Cl.
CPC ......... *G01N 33/6839* (2013.01); *G01N 21/00* (2013.01); *G01N 21/63* (2013.01);
(Continued)

(58) Field of Classification Search
CPC ........ G01N 21/00; G01N 21/33; G01N 21/63; G01N 21/77; G01N 21/78; G01N 33/68;
(Continued)

(56) References Cited

U.S. PATENT DOCUMENTS 3,632,496 A * 1/1972 Patterson et al. ........ B01J 19/08
204/249
3,694,160 A * 9/1972 Sagusa et al. ......... G01N 30/96
436/89
(Continued)

FOREIGN PATENT DOCUMENTS

EP    2735876 A1    5/2014
JP    H0628261 A    10/1994

OTHER PUBLICATIONS

Bhushan et al Biomedical Chromatography, vol. 11, 1997, pp. 286-288.*

*Primary Examiner* — Maureen Wallenhorst
(74) *Attorney, Agent, or Firm* — Kimberly A. Chasteen (57) ABSTRACT

A method for analyzing one or more nitrogen-containing compounds is disclosed. In the method, a ninhydrin-containing composition is irradiated with UV light in an activation zone to produce a ninhydrin reagent containing hydrindantin. The ninhydrin reagent is passed to a reaction zone. In the reaction zone the ninhydrin reagent is contacted with the nitrogen-containing compounds.

21 Claims, 2 Drawing Sheets

(51) Int. Cl.
*G01N 21/63* (2006.01)
*G01N 21/33* (2006.01)
*G01N 31/22* (2006.01)
G01N 21/78 (2006.01)

(52) U.S. Cl.
CPC ............ *G01N 21/33* (2013.01); *G01N 21/78* (2013.01); *G01N 31/22* (2013.01); *Y10T 436/173845* (2015.01)

(58) Field of Classification Search
CPC ........... G01N 33/6809; G01N 33/6839; G01N 31/22; Y10T 436/17; Y10T 436/173845; Y10T 436/20; Y10T 436/200833; Y10T 436/203332
USPC ... 436/35, 89, 106, 111, 127, 128, 131, 164, 436/166; 422/82.05
See application file for complete search history.

(56) References Cited

U.S. PATENT DOCUMENTS

| | | | | |
|---|---|---|---|---|
| 3,778,230 | A | * | 12/1973 | Arikawa ................ G01N 30/74 436/161 |
| 4,226,194 | A | * | 10/1980 | Grahn .................... G08B 15/02 109/25 |
| 4,274,833 | A | * | 6/1981 | Pickering ........... G01N 33/6809 210/656 |
| 2009/0155136 | A1 | | 6/2009 | Cooper et al. |

\* cited by examiner

APPARATUS AND METHOD FOR PREPARING A NINHYDRIN REAGENT

The present invention relates to a novel method for preparing a ninhydrin reagent for analysing nitrogen-containing compounds. The present invention further relates to a novel apparatus for preparing a ninhydrin reagent for analysing nitrogen-containing compounds.

Amino acids are the components from which proteins are formed, which in turn play a key role in many biological processes. In some cases the presence or absence of a particular amino acid in an individual can seriously affect their health. For example, an individual suffering from the genetic metabolic disorder phenylketonurea cannot metabolise phenylalanine, the accumulation of which severely affects their brain development. Accordingly, methods for detecting free amino acids or determining the amino acid compositions of proteins are vital for the proper diagnosis and management of diseases. Similarly, such methods are important for the analysis of commercial drugs, food and foodstuffs, as well as protein and enzyme research and development. More generally, the detection and identification of nitrogen-containing compounds finds applications across a wide range of disciplines, including agricultural, biochemical, clinical, environmental, food, forensic, histochemical, microbiological, medical, nutritional, plant and protein sciences.

In the 1950's the first automated amino acid analysis method was developed by Moore, Stein and Spackman, (Spackman D H, Stein W H, and Moore S. *Automatic recording apparatus for use in the chromatography of amino acids. Anal Chem,* 1958, 30:1190-1206). This multi-stage process involves separating the amino acids by ion exchange liquid chromatography. A ninhydrin reagent is then pumped from a reagent reservoir, mixed with the eluate from the ion exchange column and passed through a steel or plastic reaction coil, and heated to the temperature required for reaction.

The ninhydrin reagent reacts with the amino acids and related amine compounds to form highly coloured reaction products which can be further analysed using a photometer. The identity of each amino acid is established on the basis of its migration characteristics and position on the chromatogram. The concentration of each amino acid is determined by the intensity of the coloured product detected in a photometer by way of absorbance at a specified wavelength.

The colour reaction between ninhydrin and amino acids or amines is very slow at room temperature. It is significantly faster at elevated temperatures, but still takes many minutes, even at a temperature of 130° C. and above. To maintain good chromatographic performance the colour reaction needs to take place in a time period of around one minute or less. To achieve this, hydrindantin, the reduced form of ninhydrin, is required for the ninhydrin reagent to be effective and provide an acceptable rate of reaction. There have been a number of suggested reasons or mechanisms for explaining the ability of hydrindantin to speed up the formation of the coloured products at elevated temperatures. One suggestion is that hydrindantin acts as a stabiliser for one of the reaction intermediates.

Unfortunately, however, hydrindantin is particularly unstable in the presence of air, oxygen in the air rapidly oxidising the hydrindantin to ninhydrin. Only relatively small amounts of air are necessary to seriously deplete the amount of hydrindantin in the reagent and thus substantially reduce the sensitivity of the colour production in the photometric analysis. An inert atmosphere, usually nitrogen, may be used both in the preparation and during the use of the ninhydrin reagent, in an attempt to reduce the oxidation of hydrindantin. As can be appreciated, the requirement for an inert atmosphere results in the need for complex equipment and handling procedures, to ensure hydrindantin, essential for rapid amino acid analysis, does not deteriorate at an unacceptable rate before and/or during its use. In addition, hydrindantin is insoluble in totally aqueous media. Accordingly a substantial amount of organic solvent is required for storage and use of the same.

In light of the above, the method developed by Moore, Stein and Spackman utilised a reagent comprising ninhydrin and a reducing agent capable of reducing ninhydrin to form hydrindantin when required. Prior to use the ninhydrin reagent would be prepared by mixing together a sodium acetate buffer, ninhydrin and the reducing agent stannous chloride. The ninhydrin reagent would then be pumped from a reagent reservoir, mixed with the eluate from the ion exchange column and passed through a steel or plastic reaction coil, and heated to the temperature required for reaction.

A disadvantage caused by the strong reducing activity of stannous chloride, even at room temperature, is that the reagent must first be prepared in an inert container to minimise the risk of oxidation of hydrindantin. Further, stannous chloride is known to cause precipitation of tin hydroxide compounds, which can block the analytical equipment.

Alternative reducing agents to stannous chloride have since been investigated such as cyanide, titanous salts, borohydride and ascorbic acid. These strong reducing agents react instantaneously with ninhydrin to produce hydrindantin at room temperature. Cyanide could not be used commercially because of toxicity issues and lacked the necessary stability. More serious studies were carried out on sodium borohydride and ascorbic acid reducing agents. For example, U.S. Pat. No. 3,778,230 and U.S. Pat. No. 4,274,833 disclose ninhydrin reagents comprising ascorbic acid and sodium borohydride or stannous chloride as reducing agents respectively. However, these reagents must also first be prepared in an inert container at ambient temperatures to minimise risk of oxidation of hydrindantin. With particular reference to U.S. Pat. No. 3,778,230 and the use of ascorbic acid as reducing agent, a serious disadvantage is the production of coloured by-products which adversely affect the accuracy of the results.

An alternative method and the most common one used today is to add hydrindantin directly to a reagent comprising ninhydrin. No reducing agent is utilised. Once the reagent, comprising ninhydrin and hydrindantin has been formed, it can be used on the amino acid analyser.

In practice, it is impossible to completely exclude air either whilst mixing ninhydrin with existing reducing agents or during use of existing ninhydrin reagents on standard amino acid analysers. As a result, the hydrindantin concentration in existing reagents inevitably steadily decreases until no colour reaction can take place. For this reason, existing ninhydrin reagents comprising hydrindantin have a limited life of no longer than one month and sometimes as short as two weeks.

One solution is provided in U.S. Pat. No. 3,632,496. This document discloses a method and apparatus for reagents comprising ninhydrin. The apparatus comprises an elongate conduit having a channel there through, an inlet at one end for receiving a reagent and an outlet at the other end for discharging the activated reagent. The channel is defined by surfaces of metal coated resin beads capable of electrolytically reducing ninhydrin to hydrindantin. In a preferred embodiment, electrodes are provided for passing a current through the reagent which is claimed to facilitate the reduction of ninhydrin to hydrindantin.

Whilst no reducing agent is required, the method disclosed in U.S. Pat. No. 3,632,496 requires a very complex apparatus for its implementation. For example, the process for forming the metal coated resin beads is particularly complicated. In addition, the high surface area within the channel would be easily subject to contamination. Any adsorption of impurities from the reagent would affect the concentration of hydrindantin produced, leading to difficulties in obtaining accurate results. It is therefore likely that frequent replacement of the resin beads would be required, particularly when the apparatus is being used on a commercial scale or in a busy laboratory. Further, the ninhydrin reagent disclosed requires the presence of a solvent, increasing the overall cost of the reagent significantly.

Accordingly, an alternative method for preparing a ninhydrin reagent such that hydrindantin is only formed when required is necessary. It would be advantageous if such a method could be implemented using a relatively simple and inexpensive apparatus.

EP 2 735 876 is a recent publication relating to a method for analysing amino acids and a reagent for use with the same.

In a first aspect, the present invention provides a method for preparing a ninhydrin reagent for use in the analysis of nitrogen-containing compounds, the method comprising:

irradiating a ninhydrin-containing composition with UV light.

In the method of the present invention, a ninhydrin reagent is formed from a ninhydrin-containing composition as the starting material. The ninhydrin reagent formed according to the method of the present invention comprises components from the ninhydrin-containing composition and hydrindantin. The components of the ninhydrin-containing composition are described in more detail below. Once the ninhydrin reagent has been prepared according to the method of the present invention, the reagent can be used in accordance with known and standard procedures and methods for the detection of nitrogen-containing compounds, including but not limited to amino acids. The ninhydrin-containing composition does not need to comprise hydrindantin or a reducing agent, as is discussed in more detail below. In fact, in a preferred embodiment, the ninhydrin-containing composition is substantially free of hydrindantin and/or any reducing agents. As a result of this, the components of the ninhydrin-containing composition are highly stable in the presence of oxygen and therefore do not need to be stored separately and premixed just before use. The ninhydrin reagent of the present invention may be used as a visualising agent in general, provided that the test sample comprises one or more organic nitrogen containing compounds.

As discussed above, the present invention provides a method for preparing a ninhydrin reagent for use in the analysis of nitrogen-containing compounds.

The ninhydrin-containing composition used in the method of the present invention may comprise ninhydrin in any suitable amount. Preferably, the concentration of ninhydrin in the composition is from 0.1% to 5% w/v. More preferably, the concentration of ninhydrin is from 0.7 to 2.5% w/v. Yet still more preferably, the concentration of ninhydrin in the composition is from 1 to 2% w/v. In general, the amount of ninhydrin present in the composition to be processed will depend upon such factors as the concentration of hydrindantin required in the product composition and the conditions under which the composition is irradiated.

In a preferred embodiment, the ninhydrin-containing composition comprises ninhydrin and an aqueous buffer. Ninhydrin and suitable aqueous buffers are both commercially available and used in existing ninhydrin reagents.

Any suitable aqueous buffer may be used in the ninhydrin reagent. Suitable buffers are known in the art. An acidic buffer is preferred. More preferably, a weak acidic buffer is preferred, so as to maintain the pH at a value of between 3 to 7, more preferably from 4 to 6, still more preferably from 4.5 to 5.5. A particularly suitable pH is about 5.2.

The buffer may be prepared from any weak acid and one of its conjugate bases/salts. The acid may be an organic acid or an inorganic acid. Organic acids are preferred, examples of which include lower carboxylic acids, in particular carboxylic acids having from 1 to 6, more preferably from 1 to 4 carbon atoms, with acetic acid, ethanoic acid and propanoic acid being particularly preferred. One preferred combination is acetic acid and one of its salts.

The acid salt may be any suitable salt. The salt may be formed from any metal cation. Suitable salts include those having a metal cation from Group I or Group II of the Periodic Table. However it is preferable that the salt is formed from any one of the alkali metals, in particular lithium, sodium or potassium.

Hydrindantin is insoluble in a totally aqueous media. In light of this, existing ninhydrin reagents, comprising hydrindantin, cannot be manufactured or used without the presence of a substantial amount of organic solvent. It is an advantage of the present invention however, that the ninhydrin-containing composition used in the present invention to form the ninhydrin reagent need not comprise an organic solvent or mixture of organic solvents. As a consequence, the manufacturing costs are reduced, the reagent is less harmful to the environment and waste disposal procedures are simplified. Accordingly, in one embodiment, the ninhydrin-containing composition is substantially free from an organic solvent.

The absence of an organic solvent may increase the risk of precipitation of the resulting hydrindantin, thereby affecting the efficacy of the reagent when used in amino acid analysis. Notwithstanding this, the ninhydrin reagent produced by the method of the present invention provides acceptable results when used for amino acid analysis. The reason for this is discussed in more detail below.

In an alternative and preferred embodiment however, the ninhydrin-containing composition and the resulting ninhydrin reagent both comprise ninhydrin, a suitable buffer and an organic solvent or mixture of organic solvents. Organic solvents typically used in commercially available reagents and suitable for use in the ninhydrin-containing composition used in the present invention include, dimethylsulfoxide, ethylene glycol, propylene glycol, sulfolane, hydroxy ethers, such as carbitol, propylene glycol monomethyl ether and methylcellosolve and simple alcohols, such as lower alcohols having from 1 to 4 carbon atoms, in particular methanol, ethanol and propanol. The solvents may be used either alone or as mixtures of two or more solvents.

In this alternative embodiment, the total concentration of organic solvent present in the ninhydrin-containing composition will vary according to the nature of the organic solvent. In particular, the total concentration of organic solvent used will vary from 5% v/v to 75% v/v. More preferably, the total concentration of organic solvent used will vary from 25% v/v to 65% v/v. Yet still more preferably, the total concentration of organic solvent used will vary from 40% v/v to 60% v/v.

As discussed above, the method of the present invention comprises irradiating the ninhydrin-containing composition with UV light. Ninhydrin absorbs electromagnetic radiation at wavelengths in the region of 150 to 430 nm.

As discussed above, the method of the present invention comprises the step of irradiating a ninhydrin-containing composition with UV light. Any light source capable of radiating UV light may be employed. In addition, one or more UV light sources may be employed. UV radiation at one wavelength or a plurality of different wavelengths may be employed. The different wavelengths of UV radiation may be produced using a single UV source or a plurality of different sources.

In a preferred embodiment, the UV light source comprises one or more Light Emitting Diodes (LEDs), which are used to irradiate the ninhydrin-containing composition with UV light. It has been found that the use of an LED as a UV light source provides increased control over the rate of formation of hydrindantin. In particular, UV light intensity can be more easily controlled using an LED light source. Controlling UV light intensity provides enhanced control over the rate of formation of hydrindantin from ninhydrin; in particular shorter reaction times can be employed. This is particularly advantageous when using the ninhydrin reagent formed according to the method of the present invention for amino acid analysis. In fact it has been found that even low intensity UV light emitted from an LED light source induces the formation of hydrindantin sufficiently quickly for the purposes of amino acid analysis. In addition, LED's generally require less power and produce much less heat than traditional UV lamps, such as those based on mercury, deuterium, xenon and halogen gases and vapours.

The UV light source, used in the method of the present invention is employed to induce the conversion of at least a portion of the ninhydrin present within the ninhydrin-containing composition, to form hydrindantin. As discussed above, hydrindantin is required for the rapid colour forming reaction between nitrogen-containing compounds and ninhydrin. However, hydrindantin is particularly unstable in the presence of air, the oxygen in the air rapidly oxidising the hydrindantin to ninhydrin. In addition, too much hydrindantin can precipitate out of solution. It is an advantage of the method of the present invention however that the rate of hydrindantin formation can be closely controlled, so as to prevent the formation of too high concentrations of hydrindantin and avoiding the resulting adverse effects on the further processing.

The concentration of hydrindantin produced using the method of the present invention is preferably controlled such that a minimum concentration of hydrindantin is formed, but which provides maximum sensitivity during amino acid analysis. In order to obtain the minimum concentration of hydrindantin required, the ninhydrin-containing composition is irradiated with UV light for no longer than 60 minutes, more preferably up to 40 minutes, more preferably still up to 20 minutes, yet still more preferably up to 10 minutes, yet still more preferably from 2 to 10 minutes. Reaction times of less than 2 minutes may be achieved when using a higher intensity of UV radiation, for example by employing a greater number of UV light sources.

The minimum concentration of hydrindantin required will vary according to the method and equipment employed for analysing the nitrogen containing compounds. For an amino acid analysis method, using a standard amino acid analyser, a minimum concentration of from 0.01 to 0.3% w/v, more preferably from 0.05 to 0.2% w/v, more preferably still from 0.10 to 0.14% w/v, yet still more preferably at or about 0.12% w/v is required.

The above concentrations are necessary provided the ninhydrin-containing composition comprises a large amount of organic solvent, in particular at least 50% organic solvent. In cases where the ninhydrin-containing composition does not comprise an organic solvent, a minimum concentration of from 0.01 to 0.15% w/v, more preferably from 0.03 to 0.10, more preferably still from 0.06 to 0.10% w/v, yet still more preferably at or about 0.08% w/v hydrindantin is required.

As discussed above, the method of the present invention may be used to prepare a ninhydrin reagent for use in the analysis of nitrogen-containing compounds. In particular, a ninhydrin-containing composition is irradiated with UV light such that the minimum concentration of hydrindantin is formed. Once the ninhydrin reagent has been prepared according to the method of the present invention and the minimum concentration of hydrindantin has been formed, the ninhydrin reagent may be stored or used immediately in the analysis of nitrogen containing compounds. Advantageously, once the ninhydrin reagent has been prepared according to the method of the present invention, the formation of hydrindantin does not continue. This is advantageous in that the concentration of hydrindantin present within the ninhydrin reagent does not increase during storage or during use in an amino acid analysis method, providing enhanced control over the formation of hydrindantin.

The concentration of hydrindantin produced using the method of the present invention can be more easily controlled by controlling the wavelength or range of wavelengths emitted by the UV light source. When configured to emit UV light, LED's typically emit electromagnetic radiation with wavelengths in the region of 300 to 400 nm. However, it has been found that irradiating ninhydrin with wavelengths in the region of 190 nm to 430 nm, preferably 220 nm to 390 nm, more preferably in the region of 260 nm to 380 nm, more preferably still 300 nm to 380 nm, yet still more preferably 340 nm to 370 nm, yet still more preferably 350 nm to 370 nm, yet still more preferably 360 nm to 365 nm causes hydrindantin to form very rapidly. A particularly preferred wavelength is 365 nm. Accordingly, it is preferred to use a UV light source configured to emit UV light in the aforementioned wavelengths.

In addition, the concentration of hydrindantin produced using the method of the present invention can be more easily controlled by controlling the intensity of the light emitted by the UV light source. The intensity of light emitted by the UV light source can be controlled by varying the voltage and/or current supplied to the UV light source. In particular, it has been found that the use of current limited pulse width modulation is particularly effective in controlling the voltage and/or current supplied to the LED light source. Pulse width modulation techniques are known and are commonly employed.

The intensity of light emitted by the UV light source can be varied depending upon the rate at which the ninhydrin-containing composition is irradiated with UV light and also the number of light sources employed. For example, the intensity of the light emitted by the UV light source can range from 10 mW to 10,000 mW.

In a preferred embodiment, the UV light source is used to irradiate the ninhydrin-containing composition with the composition at room temperature, this being between 0° C. and 50° C., more preferably between 20° C. and 30° C., yet still more preferably between 20° C. and 25° C. In an alternative embodiment, the UV light source is used to irradiate the ninhydrin-containing composition above room temperature, for example temperatures up to and including 250° C., although this is less preferred.

In one particularly preferred embodiment, the ninhydrin-containing composition is irradiated with the composition at a temperature below 100° C.

According to a further aspect of the present invention, there is provided the use of a ninhydrin reagent obtainable by a method as hereinbefore described for the analysis of nitrogen-containing compounds, in particular amino-acid analysis.

As discussed above, existing devices for preparing or using ninhydrin reagents for use in analysing nitrogen-containing compounds, such as in amino acid analysis, are complex. This is due to the complexities involved in preparing a stable environment for the stored composition containing the unstable hydrindantin. In contrast, the method of the present invention allows for a simpler apparatus to be employed, in particular a simple apparatus to irradiate the ninhydrin-containing composition to form hydrindantin shortly before or as it is being used in the desired analysis procedure.

Accordingly, in a further aspect the present invention provides an apparatus for preparing a ninhydrin reagent for use in the analysis of nitrogen-containing compounds, the apparatus comprising:

a conduit having an inlet for receiving a ninhydrin-containing composition and an outlet for discharging a ninhydrin reagent; and a light source for irradiating the ninhydrin-containing composition within the conduit with UV light.

The present invention provides an apparatus for preparing a ninhydrin reagent for use in the analysis of nitrogen-containing compounds. Once prepared using the apparatus of the present invention, the ninhydrin reagent may be used in accordance with known and standard procedures and methods for the detection of nitrogen-containing compounds, including but not limited to amino acids.

As above, the ninhydrin reagent formed using the apparatus of the present invention comprises components from the ninhydrin-containing composition and hydrindantin. The ninhydrin-containing composition provided to the inlet of the conduit comprises ninhydrin but does not need to comprise hydrindantin or a reducing agent capable of reducing ninhydrin to form hydrindantin above. In fact in a preferred embodiment, the ninhydrin-containing composition is substantially free of hydrindantin and/or any reducing agents. The additional components of the ninhydrin-containing composition have been described above in relation to the first aspect of the present invention.

In use, the ninhydrin-containing composition is fed into the conduit via the inlet. Whilst present within the conduit, the ninhydrin-containing composition is irradiated with UV light, such that a proportion of the ninhydrin is converted to hydrindantin. Once the required amount of hydrindantin has been formed, the ninhydrin reagent, comprising a mixture of ninhydrin and hydrindantin is allowed to exit the conduit via the outlet. As discussed above the ninhydrin reagent prepared using the apparatus and method of the present invention may be used for the purposes of analysing nitrogen-containing compounds, for example amino acid analysis.

The conduit of the apparatus may be of any shape or configuration suitable for holding the ninhydrin-containing composition while it is being irradiated with UV light. Preferably, the conduit is generally elongate in form. More preferably, the conduit is shaped such that the cross section of the conduit is uniform along its length such that the rate of formation of hydrindantin can be more easily controlled. In a preferred embodiment, the conduit is provided in the form of a cylindrical tube, preferably in the form of a coiled cylindrical tube or reaction coil. A "knitted" arrangement of the cylindrical tube may also be employed to give better exposure of the ninhydrin reagent to the UV radiation.

The conduit can be formed from any material resistant to the components of the materials passing through or therein. Suitable materials are known in the art. In a preferred embodiment, the material of at least a portion of the conduit is transparent to electromagnetic radiation in the UV spectrum. Preferably, at least a portion of the conduit is formed from material transparent to electromagnetic radiation of wavelengths in the region of 150 nm to 450 nm, more preferably wavelengths in the region of 200 nm to 420 nm, more preferably at or about 365 nm. Such materials include, but are not limited to, glass, quartz and plastic.

As discussed above, whilst present within the conduit, the ninhydrin-containing composition is irradiated with UV light, such that a proportion of the ninhydrin is converted to hydrindantin. When formed from materials such as glass and/or quartz, the conduit is capable of supporting itself in the correct position, this being a position in which a portion of the conduit, more preferably the entire conduit is capable of being irradiated with UV light. However, when formed from materials such as plastic, the conduit may be unable to support itself in the correct position. Accordingly, when the conduit is formed from materials such as plastic, securing means are preferably employed to secure the conduit in the correct position.

Any means suitable for securing the conduit in the correct position may be employed. For example, the securing means can be provided in the form of a fastener capable of fixing the conduit into the correct position. Alternatively, the securing means can form a support for supporting the conduit in the correct position. The conduit may be wound around the circumference of the support and the support is placed in the correct position. The support can be of any suitable shape and size and made from any suitable material. Preferably, the support is formed from material transparent to electromagnetic radiation of wavelengths in the region of 150 nm to 450 nm, more preferably wavelengths in the region of 200 nm to 430 nm, more preferably at or about 365 nm. Such materials include, but are not limited to, glass, quartz and plastic.

In one embodiment, the support is a source of UV light and the conduit is wound around the support such that it is supported and irradiated by the support. In this embodiment, the UV light source is preferably generally elongate and cylindrical although it is to be appreciated that other shapes may be employed.

The inlet and outlet of the conduit can be formed from the same opening in the wall of the conduit. In this way, the ninhydrin-containing composition and the ninhydrin reagent respectively enter and exit the conduit via the same opening.

More preferably, the inlet and outlet are formed from different openings. In this way, a constant flow of ninhydrin-containing material into and out of the conduit can be more easily achieved. In a preferred embodiment, the conduit is elongated and cylindrical in shape, and the inlet and outlet are provided in respective end portions of the conduit.

The design of the conduit, in particular the length and internal diameter of the conduit, will vary according to the concentration of hydrindantin required for subsequent use in an amino acid analysis method. Other factors relevant to the design of the conduit include the rate of flow of the ninhydrin-containing composition through the conduit and the intensity at which the ninhydrin-containing composition is to be irradiated with UV light. These factors are all interrelated and can be varied as required.

The apparatus of the present invention comprises one or more UV light sources for irradiating the ninhydrin-containing composition with UV light. The one or more UV light sources employed can be situated within the conduit. Alternatively, and more preferably, the UV light source is situated exterior to the conduit, with the UV light passing through the wall of the conduit to irradiate the contents therein.

As discussed above the apparatus of the present invention comprises one or more light sources for irradiating the ninhydrin-containing composition with UV light. Any light source capable of radiating UV light can be used. For example a UV lamp can be employed such as those based on LEDs, mercury, deuterium, xenon, halogen and also laser diodes, among others. UV light could also be piped from a dispersive instrument such as a spectrophotometer using optical fibres. In a preferred embodiment, an LED configured to emit UV light is employed. As discussed above in relation to the first aspect of the present invention, the LED light source provides enhanced control over the rate of formation of hydrindantin. In addition, the LED light source requires less power than other sources of UV light.

The UV light source can be positioned in any way relative to the conduit. More preferably, the light source is positioned relative to the conduit such that all or the majority of the conduit is irradiated with UV light. For example, if in the case of an elongate conduit, such as a cylindrical conduit, the light source may be positioned around the periphery of said conduit. Alternatively, the conduit may be positioned around the periphery of the said light source.

As discussed above one or more UV light sources may be employed. Preferably however, a plurality of UV light sources are employed. More preferably, one or more sources of cooling, such as fans, water jackets and/or heat sinks, capable of maintaining the temperature of the one or more UV light sources, for example at room temperature are also employed. Heat sinks are particularly suited for LEDs where very little heat is actually produced during operation. Heat sinks are commonly known and are commercially available. In a preferred embodiment, the temperature of the light source is maintained between 0° C. and 50° C., more preferably between 20° C. and 30° C., yet still more preferably between 20° C. and 25° C.

In a preferred embodiment, the conduit is contained within a housing. In this way, the housing may be formed to concentrate the UV light emitted by the light source. The housing may be of any shape capable of enclosing the conduit. For example, in one embodiment the housing is square or rectangular in shape.

In this preferred embodiment, the source of UV light can be located exterior to the housing, for example on or adjacent to an external surface of the housing. At least a portion of the external surface of the housing, preferably the portion of the external surface adjacent to the UV light source, is formed from material transparent to electromagnetic radiation. In this way, UV light radiated by the UV light source may be directed towards the conduit, present within the housing. Such materials have been discussed above and include, but are not restricted to, glass, quartz and plastic. In cases where the conduit is formed from a material such as plastic, this arrangement is advantageous in that the housing be sealed and the conduit irradiated with UV light in an inert gas atmosphere, which prevents degradation of the conduit.

More preferably, the source of UV light is located between the conduit and the housing. For example, the source of UV light can be located on or adjacent to the internal surface of the housing. More preferably, the light source is positioned on or adjacent to the internal surface of the housing, such that at least a major portion or all of the conduit is irradiated by UV light. Alternatively, in the embodiment where the light source forms a support for the conduit as discussed above, the light source can be provided anywhere within the housing, for example, on or adjacent to the internal surface of the housing.

In a preferred embodiment the internal surface, more preferably the internal surfaces of the housing comprise a reflective material, to ensure that at least a major portion or all of the conduit is irradiated by UV light. Particularly preferred reflective materials include, but are not limited to, aluminium and steel and other materials having mirrored surfaces.

In a particularly preferred embodiment, a generally cylindrical conduit is contained within a housing, the housing comprising a first opening for receiving the inlet of the conduit and a second opening for receiving the outlet of the conduit. The first and second openings may be located anywhere on the housing. More preferably, the first and second openings are located on opposing sides of said housing, and the conduit extends between the first and second openings. In this way, access to the conduit from outside the housing is possible. In use, a continuous stream of the ninhydrin-containing composition may be delivered to the inlet of the conduit and discharged through the outlet of the conduit through the respective openings in the housing.

In this particularly preferred embodiment, one or more light sources are positioned adjacent to or at the internal surface of the housing, such that the UV light is directed towards the periphery of the cylindrical conduit. Alternatively, the conduit can be supported by and irradiated with UV light by the one or more light sources as discussed above. One or more heat sinks are preferably provided on a surface exterior to the housing to direct heat generated by the UV light source away from the housing.

As previously discussed, the apparatus and method of the present invention can and preferably employs a ninhydrin-containing composition comprising no hydrindantin and substantially or wholly free of organic solvents and/or reducing agents. Due to its increased stability, the ninhydrin reagent, once prepared using the apparatus and method of the present invention, may be used as a visualising agent to identify and/or quantify a wide range of nitrogen-containing compounds.

In a preferred embodiment however, the ninhydrin reagent, prepared using the apparatus and method of the present invention is used for amino acid analysis, in particular using known and standard amino acid analysers.

Accordingly, in a still further aspect, the present invention provides a method for analysing one or more nitrogen-containing compounds, in particular amino acids and the like, the method comprising:

Irradiating a ninhydrin-containing composition with UV light in an activation zone to produce a ninhydrin reagent; and contacting the ninhydrin reagent with the nitrogen-containing compounds in a reaction zone.

The steps of irradiating a ninhydrin-containing composition with UV light in an activation zone to produce a ninhydrin reagent and contacting this reagent with the nitrogen-containing compounds may be carried out in a single stage or in a plurality of separate stages.

The method of the present invention is particularly suitable for analysing nitrogen-containing compounds, in particular amino acids and compounds formed from amino acids, such as proteins, peptides, and the like.

The nitrogen-containing compounds may be present in any liquid medium or stream. Preferably, the method of the present invention is carried out using a conventional amino acid analyser. As discussed above, commercially available amino acid analysers typically separate a test sample into its amino acid constituents by ion exchange liquid chromatography. The eluted amino acids are then mixed with a ninhydrin reagent comprising hydrindantin or one or more reducing agents and heated within a reaction coil or coils to form coloured reaction products which are subjected to photometry in known manner. Accordingly, in a preferred embodiment, the nitrogen-containing compounds are present within a conventional automatic amino acid analyser and have already been separated according to characteristics such as their size, solubility, charge and/or binding affinity prior to being contacted with the ninhydrin reagent used in the method of the present invention. Standard amino acid analysers typically use chromatographic separation techniques based on ion exchange, although other forms of chromatography may be employed. Non-chromatographic techniques may also be employed.

The ninhydrin-containing composition used in the analytical method of the present invention comprises ninhydrin, preferably a suitable buffer and, optionally, one or more organic solvents. The components of the ninhydrin-containing composition have been discussed above in relation to the first aspect of the present invention. The ninhydrin reagent comprises components from the ninhydrin-containing composition and hydrindantin.

In use, the ninhydrin-containing composition is irradiated with UV light in the activation zone to produce a ninhydrin reagent comprising hydrindantin, which is then contacted with the nitrogen-containing compounds being analysed: for example nitrogen-containing compounds present in an amino acid analyser. Once contacted, the nitrogen containing compounds and ninhydrin reagent are heated in a reaction zone to produce colour forming products which can be further analysed to quantify and qualify the nitrogen-containing compounds being analysed. It has been found that irradiating the ninhydrin-containing composition with UV light, in particular in accordance with the present invention, for example prior to contacting with the nitrogen-containing compounds, provides excellent results, despite the ninhydrin-containing composition comprising no hydrindantin and/or reducing agents.

As discussed above, the ninhydrin reagent comprising hydrindantin is contacted with the nitrogen-containing compounds to be analysed.

In one embodiment, the method of the present invention is carried out using an amino acid analyser in conjunction with an activation zone in the form of the apparatus of the further aspect of the present invention; the features of which have been described above. In this way, no modification to the amino acid analyser is necessary.

In use, a ninhydrin-containing composition is fed into the activation zone, irradiated with UV light to form a ninhydrin reagent comprising hydrindantin. Once the required concentration of hydrindantin has been produced, the ninhydrin reagent is collected from the outlet of the activation zone. In one embodiment, the ninhydrin reagent is stored in a container or the like and subsequently injected online into the amino acid analyser. The ninhydrin reagent can then be injected online into the standard amino acid analyser downstream of the chromatographic separation column to mix with the eluted amino acids prior to being heated in the heated reaction zone. Alternatively, the ninhydrin reagent can be injected online into the heated reaction zone of the amino acid analyser to mix with the eluted amino acids therein.

In an alternative embodiment, the method of the present invention is carried out using an amino acid analyser which has been modified to comprise an activation zone in the form of the apparatus of the further aspect of the present invention to provide a means for producing a ninhydrin reagent upstream of the reaction zone in the analyser. In this alternative embodiment, the ninhydrin reagent formed in the activation zone by the method of the present invention may be used directly in the analyser. In this alternative embodiment, a constant flow of ninhydrin-reagent containing hydrindantin may be formed in the activation zone and delivered to the analyser.

In this alternative embodiment, the activation zone and the reaction zone may be housed within a single chamber or vessel or may be housed within separate vessels. As noted above, the apparatus of the present invention provides a means for modifying an existing analyser, for example by adding the activation zone to the pre-existing reaction zone within the analyser.

The activation zone and the reaction zone can be contained within a single chamber, the activation zone being located upstream of the reaction zone. In this arrangement, the conditions, such as temperature and residence time, prevailing with the activation zone and the reaction zone may be the same or may be different, to optimise the reactions taking place in each zone. In this arrangement, the chamber is located downstream of the chromatographic separation column.

In use, the ninhydrin-containing composition can be injected online, upstream of the chamber. The ninhydrin-containing composition is then fed into the activation zone of the chamber and irradiated with UV light. Once the required amount of hydrindantin has been formed, the ninhydrin reagent is fed into the adjacent heated reaction zone to react with the nitrogen containing compounds being analysed. Alternatively, the ninhydrin-containing composition can be fed directly into the activation zone. The eluted amino acids can be fed upstream of the activation zone to mix with the ninhydrin-containing composition. Alternatively, the eluted amino acids can be fed directly into the activation zone to mix with the ninhydrin-containing composition. More preferably, the eluted amino acids are fed directly into the heated reaction zone to mix and react with the ninhydrin reagent.

As discussed above, the activation zone can be contained within a separate chamber to that of the reaction zone, in which case, the activation zone is located upstream of the reaction zone. In this arrangement, the activation zone and the chromatographic separation column are both located upstream of the reaction zone. In this arrangement, conditions, such as temperature and residence time, prevailing within the activation zone and the reaction zone may be more easily varied and controlled independently, offering improved versatility in terms of controlling the formation of hydrindantin in the activation zone and the subsequent reaction with nitrogen-containing compounds in the reaction zone.

In this arrangement, the activation zone is separate from the reaction zone and is in the form of the apparatus of the further aspect of the present invention; the features of which have been discussed above. In use, the ninhydrin containing composition can be injected online, upstream of the activation zone. The ninhydrin-containing composition is then fed into the activation zone and irradiated with UV light. Once the required amount of hydrindantin has been formed, the ninhydrin reagent is fed into the heated reaction zone to react with the nitrogen containing compounds being analysed. Alternatively, the ninhydrin-containing composition can be fed directly into the activation zone. The eluted amino acids can be fed upstream of the activation zone. Alternatively, the eluted amino acids can be fed directly into the activation zone to mix with the ninhydrin-containing composition. More preferably, the eluted amino acids are fed online, downstream of the activation zone to react with the ninhydrin reagent.

The components of the ninhydrin-containing composition, used in the method of the present invention, may be delivered to the activation zone separately. For example, the ninhydrin, buffer and optionally one or more organic solvents may be drawn from separate containers or reservoirs by respective pumps and delivered to a common line or mixing zone, where they are combined to form a mixture before entering the activation zone. This mixture is then delivered to the activation zone. Alternatively, the ninhydrin, buffer and optionally one or more organic solvents are drawn from separate containers or reservoirs by respective pumps and delivered to the activation zone directly, where they are combined to form a mixture.

More preferably, however, the ninhydrin, buffer and optionally one or more organic solvents are delivered upstream of the activation zone or directly into the activation zone together as a mixture. This technique is simpler to employ and requires only a very simple apparatus. Further, the components of the ninhydrin-containing composition that can be employed in the method of the present invention are such that the composition is very stable. Accordingly, the composition may be prepared well in advance of being used and stored very easily in a single bottle. Advantageously, the ninhydrin-containing composition may be stored indefinitely, even in the presence of air and at room temperature.

As discussed above, the ninhydrin reagent is irradiated in the activation zone such that the required amount of hydrindantin is formed for subsequent use in the reaction zone. As discussed above, the required amount of hydrindantin formed is such that it provides good sensitivity but does not precipitate out of solution. The rate at which hydrindantin is formed will vary mainly according to the duration and intensity of irradiation within the activation zone. The conditions for forming hydrindantin in the activation zone from the ninhydrin-containing composition are as described above in relation to the first aspect of the present invention.

In the method of the further aspect of the present invention, it is particularly preferred to maintain the temperature within the activation zone at or about room temperature, this being between 0° C. and 50° C., more preferably between 20° C. and 30° C., yet still more preferably between 20° C. and 25° C. Temperatures above room temperature may be employed, for example up to and including 250° C. In a preferred embodiment, temperatures below 100° C. are employed.

Where the temperature within the activation zone is maintained above room temperature, in order to keep the temperature constant within the activation zone a thermostatically controlled heater is preferably utilised. In addition, the one or more UV light sources and heat sinks discussed in relation to the apparatus of the further aspect of the present invention are preferably situated outside the activation zone or at a short distance there from.

The reaction zone is used so that the ninhydrin reagent containing hydrindantin can react with the nitrogen-containing compounds, such as one or more amino acids, at an elevated temperature to form Ruheman's Purple. By controlling the rate of formation of hydrindantin in the activation zone, the final concentration of hydrindantin present in the reaction zone can be closely regulated. Advantageously, once the required concentration of hydrindantin has been formed in the activation zone and the ninhydrin reagent is fed into the reaction zone, the formation of hydrindantin does not continue. More significantly, the temperature within the reaction zone is not constrained by the need to form hydrindantin in the required concentration, this having been already achieved in the activation zone. In this way, the conditions in the reaction zone can be optimised for analysis of the nitrogen-containing compounds, in particular the colour forming reactions with amino acids.

The reaction zone may be of any suitable configuration to allow the activated ninhydrin reagent containing hydrindantin to react with the nitrogen-containing compounds being analysed. Suitable configurations for the reaction zone include the colour forming reaction chamber of existing amino acid analysers, that is, in the form of a coil or column.

All existing amino acid analysers have means to vary the temperature within the reaction zone to optimise the colour-forming reaction between the ninhydrin reagent and the nitrogen containing compounds. Preferably the temperature within the reaction zone is in the range of from 100° C. to 160° C., still more preferably from 115° C. to 145° C., more preferably still from 120° C. to 135° C.

The residence or dwell time of the components in the reaction zone may also be varied, to optimise the colour-forming reaction between the ninhydrin reagent and the nitrogen containing compounds. For example, the dwell time may be varied according to the amount of hydrindantin formed in the activation zone. Preferably, the dwell time in the reaction zone is in the range of from 10 to 180 seconds, more preferably from 20 to 80 seconds, still more preferably from 30 to 60 seconds.

Embodiments of the present invention will now be described by way of example only, having reference to the accompanying drawings, in which.

Figure 1:
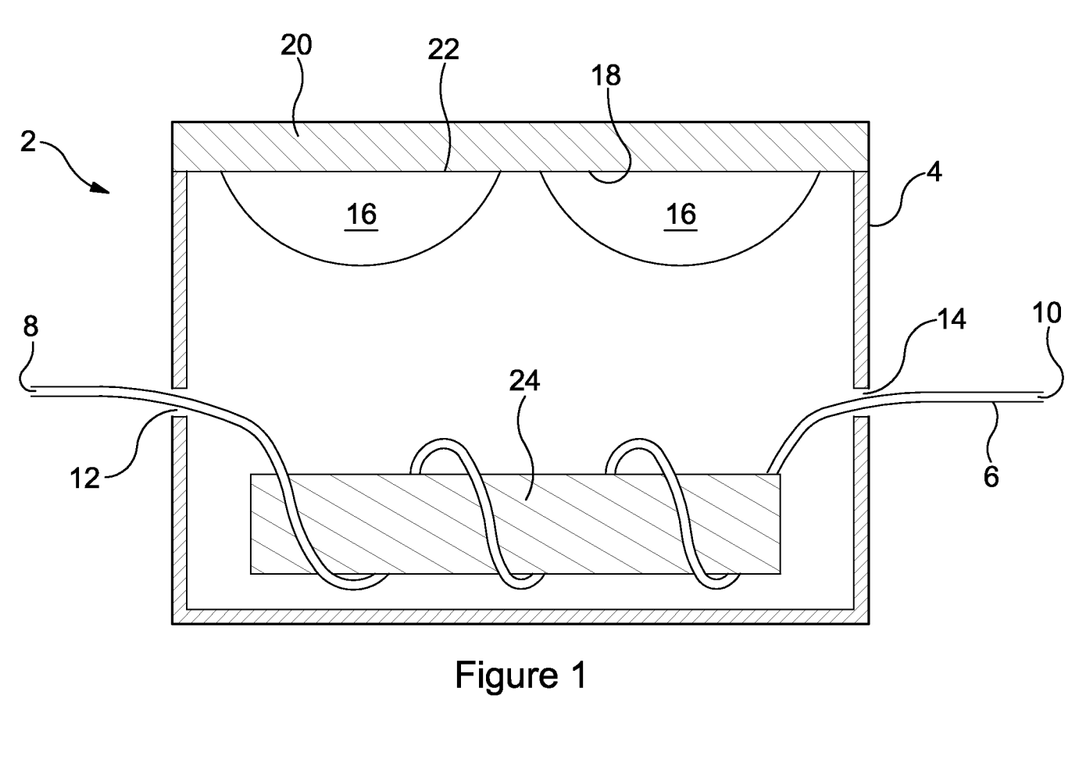
FIG. 1 is a longitudinal cross-sectional view of an apparatus according to a preferred embodiment of the first aspect of the present invention.

Referring to FIG. 1, there is shown an apparatus, generally indicated as 2 for irradiating a nitrogen-containing composition with UV light. The apparatus 2 comprises a housing 4, the housing 4 comprising a conduit 6. The conduit 6 comprises an inlet 8 for receiving a ninhydrin-containing composition and an outlet 10 for discharging a hydrindantin-containing composition. As shown, the conduit 6 is generally cylindrical in shape.

The housing 4 further comprises a first opening 12 for receiving the inlet 8 of the conduit 6 and a second opening 14 for receiving the outlet 10 of the conduit 6. As shown, the conduit 6 extends between the first and second openings 12, 14 of the housing 4. In this way, access to the conduit 6 from outside the housing 4 is possible. In use, a continuous stream of the ninhydrin-containing composition may be delivered to the inlet 8 of the conduit 6 and discharged through the outlet 10 of the conduit 6 through the respective openings (12 and 14) of the housing 4.

Whilst present within the conduit 6, the ninhydrin-containing composition is irradiated with UV light, such that a proportion of the ninhydrin is converted to hydrindantin. In this respect, the housing 4 comprises one or more UV light sources 16, for radiating the ninhydrin-containing composition within the conduit 6 with UV light. As shown, the one or more UV light sources 16 are situated exterior to the conduit 6, on or adjacent to the internal surface 18 of the housing 4, such that the UV light is directed towards the periphery of the conduit 6. The internal surface 18 of the housing 4 comprises a reflective material, to ensure that at least a major portion, more preferably all of the conduit is irradiated by UV light. The apparatus 2 further comprises one or more heat sinks 20 for maintaining the temperature of the one or more UV light sources at room temperature. One or more heat sinks are provided on the external surface 22 of the housing 4 to direct heat generated by the one or more UV light sources 16 away from the housing 4.

In FIG. 1, the conduit 6 is made from a material such as plastic and is therefore unable to support itself in the correct position, that being the position in which at least a portion of the conduit 6, more preferably the entire conduit 6, is capable of being irradiated with UV light. Accordingly, as shown, the conduit 6 is wound around a support member 24 for supporting the conduit 6 in the correct position. The support member 24 is generally cylindrical in shape and is positioned directly underneath the one or more UV light sources 16.

Figure 2:
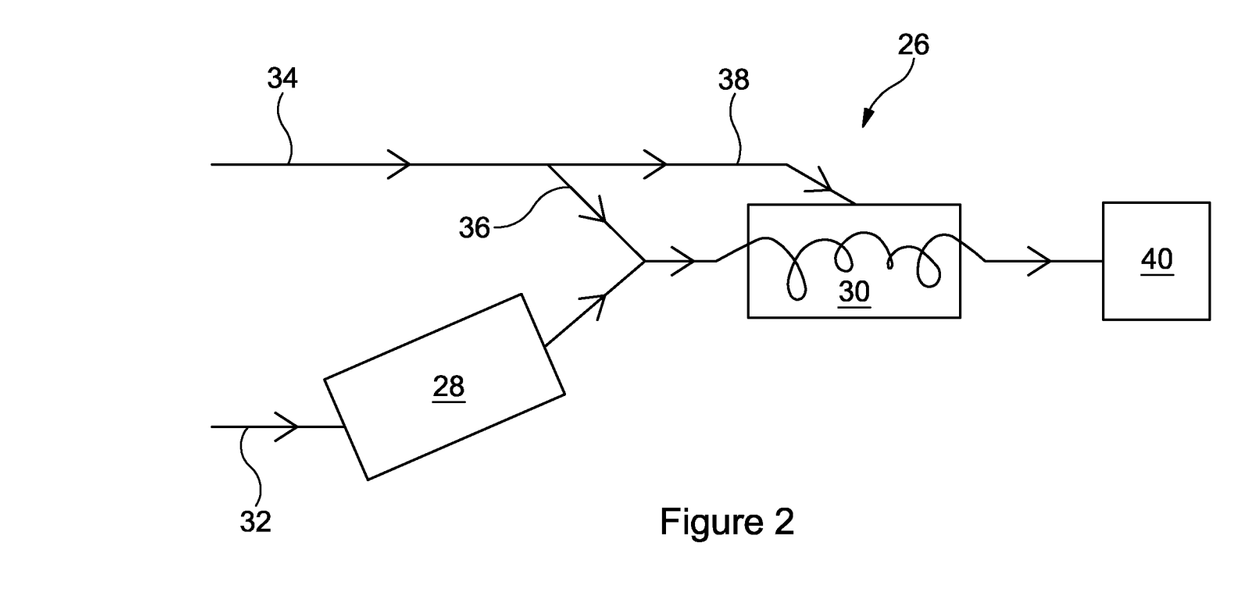
FIG. 2 is a flow diagram illustrating an amino acid analyser for carrying out the method of a further aspect of the present invention.

Referring to FIG. 2, there is shown an amino acid analyser for carrying out the method of the present invention, generally indicated as 26. The amino acid analyser 26 does not show the means for separating the amino acid sample into its constituent components. However, as discussed above, various known techniques for separating amino acids may be employed. The amino acid analyser 26 comprises an activation zone 28 for irradiating a ninhydrin containing composition with UV light and a reaction zone 30, used to react the hydrindantin-containing composition so produced with nitrogen-containing compounds at an elevated temperature.

The activation zone 28 and reaction zone 30 are arranged according to a preferred embodiment of the present invention, wherein the activation zone 28 is contained within a separate chamber or vessel to that of reaction zone 30 and is located upstream of the reaction zone 30. In an alternative arrangement, the activation zone 28 and the reaction zone 30 are within a single chamber or vessel, with the activation zone 28 comprising an upstream region of the chamber or vessel and the reaction zone 30 comprising a downstream region of the chamber or vessel.

The amino acid analyser 26 further comprises a first feed line 32. The first feed line 32 is located upstream of the activation zone 28 and is used to deliver the ninhydrin-containing composition into the amino acid analyser 26. In this embodiment, the components of the ninhydrin-containing composition are delivered to the activation zone 28 together as a mixture. The activation zone 28 irradiates the ninhydrin-containing composition with UV light at room temperature for a pre-determined period of time. The hydrindantin-containing composition so produced is then delivered to the reaction zone 30.

The amino acid analyser 26 further comprises a second feed line 34. The second feed line 34 delivers the amino acids into the amino acid analyser 26. The second feed line 34 delivers the amino acids to a site downstream of the activation zone 28 but upstream of the reaction zone 30, indicated as 36. In an alternative embodiment indicated as 38, the second feed line 34 delivers the amino acids directly to the reaction zone 30.

The reaction zone 30 heats the activated ninhydrin reagent and amino acids to an elevated temperature for a predetermined period of time. The reaction products are delivered to a photometer 40 where the concentration and characteristics of the amino acids is detected and measured.

EXAMPLE

An apparatus according to FIG. 1 was used to form a ninhydrin reagent comprising hydrindantin for use on an amino acid analyser. The apparatus comprised 4 high efficiency UV LEDs; the optical characteristics of each LED at 25° C. being as follows:

Peak wavelength: 365 nm
Radiant flux (intensity) at 700 mA: 320 mW
Viewing angle ($2\theta_{1/2}$): 85°
Total included angle ($\theta_{0.9V}$): 100°

The intensity of each LED was controlled using pulse width modulation at a fixed current of 360 mA. In use, the pulse width could be varied between 0% and 100%, providing a maximum total intensity range of 658 mW radiant flux.

The characteristics of the conduit (reaction coil) were as follows;

Internal diameter: 0.15 cm
Length: 1.7 meters

Two experiments were conducted, one in which a ninhydrin-containing composition comprising an organic solvent was irradiated with UV light using the apparatus according to FIG. 1 and another in which a ninhydrin-containing composition comprising no organic solvent was irradiated with UV light using the apparatus according to FIG. 1. The results of these two experiments are as follows;

Example 1—Ninhydrin-Containing Composition Comprising an Organic Solvent

A ninhydrin-containing composition comprising 2% w/v ninhydrin, 50% w/v ethylene glycol and 1M sodium acetate buffer adjusted to pH 5.2 was irradiated with UV light using the apparatus according to FIG. 1. The flow rate through the conduit (reaction coil) was set at 0.30 ml/min giving a residence time in the apparatus of 10 minutes. The pulse width modulation was set at 35% giving a total radiant flux intensity of 230 mW. A hydrindantin concentration of 0.12% w/v was obtained in the resulting product.

Example 2—Ninhydrin-Containing Composition without Organic Solvent

A ninhydrin-containing composition comprising 2% w/v ninhydrin and 1M sodium acetate buffer adjusted to pH 5.2 was radiated with UV light using the apparatus according to FIG. 1. The flow rate through the conduit (reaction coil) was set at 0.30 ml/min giving a residence time in the apparatus of 10 minutes. The PWM was set at 25% giving a total radiant flux intensity of 165 mW. A hydrindantin concentration of 0.08% w/v was obtained in the resulting product.

It is to be appreciated that the concentration of hydrindantin produced can be varied, for example, by increasing or decreasing the concentration of ninhydrin, the flow rate, the length of the conduit, the number of LED light sources and the intensity at which they radiate UV light.

The invention claimed is:

1. A method for analysing one or more nitrogen-containing compounds, the method comprising:
   irradiating a ninhydrin-containing composition with UV light in an activation zone to produce a ninhydrin reagent comprising hydrindantin;
   passing the ninhydrin reagent to a reaction zone; and
   contacting the ninhydrin reagent with the nitrogen-containing compounds in the reaction zone.

2. The method according to claim 1 wherein the activation zone is at a temperature below 100° C.

3. The method according to claim 1, wherein the reaction zone is at a temperature in the range of from 100° C. to 160° C.

4. The method according to claim 1, wherein the ninhydrin reagent and the nitrogen-containing compounds have a residence or dwell time in the reaction zone in the range of from 10 to 180 seconds.

5. The method according to claim 1, wherein ninhydrin is present in the ninhydrin-containing composition in an amount of from 0.1% to 5% w/v.

6. The method according to claim 1, wherein the ninhydrin-containing composition comprises an aqueous buffer.

7. The method according to claim 6, wherein the aqueous buffer comprises a weak acid and one of its conjugate bases/salts.

8. The method according to claim 6, wherein the aqueous buffer maintains a pH value of the ninhydrin-containing composition of between 3 to 7.

9. The method according to claim 1, wherein the ninhydrin-containing composition further comprises one or more organic solvents.

10. The method according to claim 9, wherein the organic solvent is selected from the group consisting of dimethylsulfoxide, ethylene glycol, propylene glycol, sulfolane, carbitol, propylene glycol monomethyl ether, methylcellosolve, methanol, ethanol and propanol.

11. The method according to claim 9, wherein organic solvent is present in an amount of from 5% v/v to 75% v/v.

12. The method according to claim 1, wherein the ninhydrin-containing composition does not comprise hydrindantin or a reducing agent.

13. The method according to claim 1, wherein hydrindantin is present in the ninhydrin reagent in an amount of from 0.01 to 0.3% w/v.

14. The method according to claim 1, wherein hydrindantin is present in the ninhydrin reagent in an amount of from 0.01 to 0.15% w/v.

15. The method according to claim 1, wherein one or more UV light sources are used to irradiate the ninhydrin-containing composition with UV light.

16. The method according to claim 15, wherein the UV light source is configured to emit UV light with wavelengths in the range of from 190 nm to 430 nm.

17. The method according to claim 16, wherein the UV light source is configured to emit UV light with wavelengths in the range of from 350 nm to 370 nm.

18. The method according to claim 17, wherein the UV light source is configured to emit UV light with a wavelength of 365 nm.

19. The method according to claim 15, wherein the UV light source emits UV light at an intensity in the range of from 10 mW to 10,000 mW.

20. The method according to claim 1, wherein the ninhydrin-containing composition is irradiated with UV light at a temperature below 100° C.

21. The method according to claim 20, wherein the ninhydrin-containing composition is irradiated with UV light at a temperature of from 20° C. to 25° C.

* * * * *